United States Patent
Glatkowski et al.

(10) Patent No.: US 7,342,479 B2
(45) Date of Patent: Mar. 11, 2008

(54) SENSOR DEVICE UTILIZING CARBON NANOTUBES

(75) Inventors: Paul J. Glatkowski, Littleton, MA (US); David H. Landis, Jr., Barrington, RI (US); Joseph W. Piché, Raynham, MA (US)

(73) Assignee: Eikos, Inc., Franklin, MA (US)

( * ) Notice: Subject to any disclaimer, the term of this patent is extended or adjusted under 35 U.S.C. 154(b) by 85 days.

(21) Appl. No.: 10/833,274

(22) Filed: Apr. 28, 2004

(65) Prior Publication Data

US 2005/0000830 A1 Jan. 6, 2005

Related U.S. Application Data

(60) Provisional application No. 60/465,796, filed on Apr. 28, 2003.

(51) Int. Cl.
*H01C 7/00* (2006.01)

(52) U.S. Cl. .......................... 338/34; 338/14; 436/169; 205/501

(58) Field of Classification Search ............ 338/13–14, 338/25–28, 34–35; 436/169; 204/451; 205/501; 422/83; 604/20, 113; 128/898
See application file for complete search history.

(56) References Cited

U.S. PATENT DOCUMENTS

| | | | |
|---|---|---|---|
| 2003/0032892 A1* | 2/2003 | Erlach et al. ............... | 600/547 |
| 2003/0109056 A1* | 6/2003 | Vossmeyer et al. ......... | 436/169 |
| 2004/0067530 A1* | 4/2004 | Gruner ....................... | 435/7.1 |
| 2004/0076681 A1* | 4/2004 | Dennis et al. .............. | 424/489 |
| 2004/0106213 A1* | 6/2004 | McLaughlin et al. ....... | 436/171 |

OTHER PUBLICATIONS

U.S. Appl. No. 60/378,843, (Electronic Sensing of Biomolecular Processes), pp. 1-7, 4 drawing sheets (FIGs 1a-c and 2) filed May 8, 2002.*

Collins, G. Philip, et al., "Extreme Oxygen Sensitivity of Electronic Properties of Carbon Nanotubes," Science, 287:1801-1804, Mar. 10, 2000.

Cui, Yi, et al., "Nanowire Nanosensors for Highly Sensitiive and Selective Detection of Biological and Chemical Species," Science, 293:1289-1292, Aug. 17, 2001.

King, Jing, et al., "Nanotube Molecular Wires as Chemical Sensors," Science, 287:622-625, Jan. 28, 2000.

* cited by examiner

*Primary Examiner*—K. Richard Lee
(74) *Attorney, Agent, or Firm*—Novak Druce & Quigg LLP

(57) ABSTRACT

Chemical sensors for detecting analytes in a fluid is disclosed. The chemical sensors include chemically sensitive resistors that utilize carbon nanotubes as a chemically sensitive element. The disclosed sensors additionally utilize polymers which selectively alter or inhibit the chemical sensitivity of the carbon nanotubes. Methods of preparing the sensors as well as methods of their use are also disclosed.

16 Claims, No Drawings

SENSOR DEVICE UTILIZING CARBON NANOTUBES

REFERENCE TO RELATED APPLICATIONS

This application claims priority to U.S. Provisional Application No. 60/465,796, of the same title filed Apr. 28, 2003, the entirety of which is hereby incorporated by reference.

BACKGROUND

1. Field of the Invention

This invention is directed to sensor devices that utilize carbon nanotubes as a chemically sensitive element and methods for using carbon nanotubes as a chemically sensitive element. The invention is also directed to methods of making devices with carbon nanotubes as a chemically sensitive element.

2. Description of the Background

Techniques and devices for detecting a wide variety of analytes in fluids such as vapors, gases and liquids are known. As used herein the term "fluid" means gases, vapors and liquids. An electronic nose is an instrument used to detect vapors or chemical analytes in gases, solutions, and solids. In certain instances, the electronic nose is used to simulate a mammalian olfactory system. In general, an electronic nose is a system having an array of sensors that are used in conjunction with pattern-recognition algorithms. Using the combination of chemical sensors, which produce a fingerprint of the vapor or gas, the recognition algorithms can identify and/or quantify the analytes of interest. The electronic nose is thus capable of recognizing unknown chemical analytes, odors, and vapors.

In practice, an electronic nose is presented with a substance such as an odor or vapor, and the sensor converts the input of the substance into a response, such as an electrical response. The response is then compared to known responses that have been stored previously. By comparing the unique chemical signature of an unknown substance to "signatures" of known substances, the unknown analyte can be determined. A variety of sensors can be used in electronic noses that respond to various classes of gases and odors.

A typical type of sensor is disclosed in U.S. Pat. No. 5,571,401, issued to Lewis et. al; the disclosure of this application is hereby incorporated by reference. Devices utilizing the sensor disclosed by Lewis et. al. are described in U.S. Pat. Nos. 6,450,008; 6,422,061; 6,418,783; 6,085,576; 6,234,006; and 6,319,724 and U.S. Published patent application Ser. Nos. 09/796,877; 10/099,405; 10/174,633; and 10/153,883, the disclosure of these patents and applications are hereby incorporated by reference.

The sensors disclosed by Lewis et al. are individual thin-film carbon-black polymer composite chemiresistors configured into an array. The collective output of the array can be used to identify an unknown analyte using standard data analysis techniques. Each individual detector of the sensor array is a composite material consisting of conductive carbon black homogeneously blended throughout a non-conducting polymer.

The detector materials are deposited as thin films on an alumina substrate each across two electrical leads creating conducting chemiresistors. The output from the device is an array of resistance values as measured between each of the two electrical leads for each of the detectors in the array.

When a composite is exposed to a vapor-phase analyte, the polymer matrix acts like a sponge and "swells up" while absorbing the analyte. The increase in volume is concomitant with an increase in resistance because the conductive carbon-black pathways through the material are broken. When the analyte is removed, the polymer "sponge" off-gasses and "dries out". This causes the film to shrink and the conductive pathways are reestablished. The baseline resistance (Rbaseline) of the device is measured while a representative background vapor flows over the array. The response from the chemiresistor during an analyte exposure is measured as a bulk relative resistance change ($\Delta R_{max}/R_{baseline}$). Since an analyte will absorb into the different polymer matrices to different degrees, a pattern of response is observed across the array.

The relationship between volume increase and the resistance change in these composite films can be described by percolation theory. See Lonergan, M. C.; Severin, E. J.; Doleman, B. J.; Beaber, S. A.; Grubbs, R. H.; Lewis, N. S. Chem. Mater. 1996, 8, 2298. Percolating networks are ubiquitous in nature and are based on the idea that certain phenomena propagate through a system by interactions between neighboring active sites. Examples include forest fires spreading from tree to tree, disease spreading through a population by human contact, sol-gel transitions in biopolymer gelation, and, as in this case, resistor networks that are either continuous, and connected, or discontinuous. (See Stauffer, D.; Aharony, A.; Introduction to Percolation Theory; Taylor & Francis: Bristol, Pa., 1994).

In percolating resistor networks, there is a critical point where the last conductive pathway is broken and the system becomes discontinuous. This point is called the percolation threshold and is highly dependent on system variables. In the case of carbon black polymer composites, the percolation threshold is reached when an individual detector's resistance sharply increases with a small increase in volume of the composite film. The form of a percolation curve is very similar to a pH titration curve. The change in volume required to reach the percolation threshold for a given detector is dependent on the amount of carbon black in the polymer matrix, the structure of that carbon black, the degree of contact between carbon black clusters, and how homogeneously dispersed are the carbon black clusters through the matrix.

The polymer matrix "swells up" because analyte vapor absorbs into the film to an extent determined by the partition coefficient of the analyte. The partition coefficient defines the equilibrium distribution of an analyte between the vapor phase and the condensed phase at a specified temperature. This is expressed as: $K=C_s/C_v$ (1); where $C_v$ is the concentration of the analyte in the vapor phase, and $C_s$ is the concentration of the analyte in the condensed phase, which is also proportional to the detector's response. Therefore, the larger an analyte's partition coefficient, the more it will absorb into a polymer film, and the larger will be the detector's response.

Each individual detector element requires a minimum sorbed amount of analyte ($C_{s,min}$) to cause a response noticeable above the baseline noise. However, the minimum vapor concentration ($C_{v,min}$) needed to produce $C_{s,min}$ is different for each analyte since the partition coefficient is different for each analyte. Moreover, it can be shown with standard thermodynamic arguments, that the magnitude of response of an individual detector can be predicted to first order by the fractional vapor pressure exposed to the detector irrespective of the analyte identity. See Atkins, P. W.; Physical Chemistry; W. H. Freeman and Co.: New York, N.Y., 1994; and Doleman, B. J.; Severin, E. J.; Lewis, N. S. Proc. Natl. Acad. Sci., USA 1998, 95, 5442. Therefore, the general detection limit of a sorption device is best expressed as a minimum fraction of equilibrium vapor pressure rather than a concentration value.

The behavior of the detector to be sensitive to the fractional vapor pressure of the analyte it is exposed to explains why sorption devices are generally rather insensitive, in terms of concentration, to high vapor pressure analytes like methane (which is a gas at ambient temperatures) and diethyl ether, but show good sensitivity, in terms of concentration, to low vapor pressure compounds exposed at low concentrations such as volatile fatty acids. For example, if the limit of detection were 0.1% of an analyte's vapor pressure, this would indicate a detection limit of 74 ppm for ethanol, but only 0.5 ppm for nonanal (a common taint in packaging materials) at 24° C. All analytes will have roughly the same limit of detection when expressed as a fractional vapor pressure.

The differences between detector responses when exposed to a given analyte—which are required to uniquely identify that analyte by providing a unique response pattern—are due to differences in chemical interactions between the analyte and the detector films. Therefore, the limit of discrimination between two analytes exposed at the same fractional vapor pressure is determined by their relative collective chemical differences across the array. This indicates the need for as much chemical diversity as possible in the polymers comprising the array detectors for a general-purpose electronic nose. Moreover, for well-defined applications, the polymers used in the detector array can be chosen to maximize chemical differences between target analytes to increase the discrimination power of a smaller array.

As previously discussed, although the sensors disclosed by Lewis et al. work relatively well for low vapor pressure/large molecule analytes the sensors are relatively insensitive to high vapor pressure/small molecule analytes. Accordingly, a need exists for a sensor that is more sensitive to small molecule analytes.

The conductivity of carbon nanotubes is known to change with exposure to oxygen. For example, as part of a broad program investigating the synthesis, characterization and theoretical modeling of carbon nanotubes, scientists with the U.S. Department of Energy's Lawrence Berkeley National Laboratory (Berkeley Lab) and the University of California at Berkeley have reported that the electronic properties of these tubes are so "extremely sensitive" to oxygen that exposure to air can convert a semiconducting nanotube into a metallic conductor.

"Many supposedly intrinsic properties measured on nanotubes may be severely compromised by extrinsic air exposure effects," the scientists state. See Collins et al., "Extreme Oxygen Sensitivity of Electronic Properties of Carbon Nanotubes", *Science* 2000 287: 1801-1804.

One of the co-authors of the Science article stated that "We've demonstrated that carbon nanotubes can behave as both n-type and p-type semiconductors. Until now, all nanotube measurements had suggested p-type conducting behavior only." In the *Science* article, the Berkeley researchers describe that the degree of oxygen exposure is the determining factor as to whether a carbon nanotube functions as an n-type or p-type semiconductor.

Another one of the *Science* article's co-authors suggests that in principle, a nanotube's electronic properties could be controlled through the use of "protective coatings" to shield select portions of the nanotube from oxygen exposure."

Prevailing theories have held that the electronic properties of a nanotube are dictated solely by the diameter and chirality (geometric configuration) of the tube. Theories also predicted that natural defects in the hexagonal web of a nanotube's carbon atoms (nanotubes are essentially tiny sheets of graphite that have been curled and connected along a seam like a drinking straw) would give rise to the creation of atomic-sized electronic devices, a prediction that experiments in 1997 by Zettl and Collins, both authors of the Science article, confirmed.

In their latest study, Zettl and his associates found that the chemical environment surrounding a nanotube is at least as important an influence on the tube's electronic properties as its diameter. Working with single-walled carbon nanotubes (SWNTs) grown by conventional laser ablation methods, the researchers studied both bulk samples and single isolated tubes. Measurements of both electrical resistance and thermoelectric power, the voltage induced by a temperature gradient, were made under environmental conditions that gradually shifted from oxygen to vacuum and back to oxygen.

"The effects of oxygen exposure became increasingly more irreversible (and have longer time constants) with decreasing temperature, as expected for a gas adsorption process," the scientists state in the *Science* article. "In fact, our transport measurements indicate that, once SWNTs have been exposed to oxygen, it is not possible to fully deoxygenate them at room temperature even under high vacuum conditions."

Further evidence that the effects being observed were the result of gas adsorption came when the topology of the nanotubes was changed. Dilute SWNT thin films yielded quick electronic changes, while optically thick films required higher temperatures and longer times to reach equilibrium.

The experiments were repeated with different major gas constituents of air to confirm that the changes in electronic properties were due to oxygen adsorption. Carbon materials such as charcoal are known for their excellent adsorption and sieving properties, but nanotubes were thought to have been an exception because of their morphology, especially the smoothness of their exterior surface. However, a sensor utilizing carbon nanotubes to sense the presence of various chemical species has not yet been accomplished.

SUMMARY OF THE INVENTION

As embodied and broadly described herein, the present invention is directed to sensor devices comprising carbon nanotubes.

One embodiment of the invention is directed to chemically sensitive resistors comprising a resistive region comprising carbon nanotubes; and a conducting electrode on a side of the resistive region, wherein the resistance of the resistive region changes with exposure to an analyte. The resistive region may comprises only carbon nanotubes or carbon nanotubes in combination with a polymer that swells or reacts to the analyte. The change in resistance of the resistive region may comprises gross or subtle changes, such as, for example, changes of 10 fold or less, 20% or less, or 0.001% or less. Changes may also be increases in resistance across the resistive region such as, for example, changes of 0.1% or more, 10% or more or 10 fold or more. Analytes that can be detected by such resistors include organics, alkanes, alkenes, alkynes, dienes, alicyclic hydrocarbons, arenes, alcohols, ethers, ketones, aldehydes, carbonyls, water, humidity, gels, aerosols, carbanions, polynuclear aromatics and derivatives thereof, carbon dioxide gas, atmosphere, oxygen, nitrogen, halides and halide derivatives, biomolecules, sugars, isoprenes and isoprenoids, fatty acids and derivatives and combinations thereof.

Another embodiment of the invention is directed to methods for detecting an analyte comprising contacting a resistor of the invention with an area to be monitored and detecting the presence or absence of the analyte. Preferably the area comprises an enclosed region such as a box, a room, a tanker, an outside environment, a building, a body of water, a house, a body, and combinations thereof.

Other embodiments and advantages of the invention are set forth in part in the description, which follows, and in part, may be obvious from this description, or may be learned from the practice of the invention.

DESCRIPTION OF THE INVENTION

As embodied and broadly described herein, the present invention is directed to sensor devices that utilize carbon nanotubes in chemically sensitive elements and methods for making and using chemically sensitive elements using carbon nanotubes. Since carbon nanotubes are responsive to small chemical species that typical sensors have trouble detecting, the present sensors can be used to detect a wide variety of previously difficult or undetectable analytes.

Particularly, the invention provides chemically sensitive resistors that can be used, for example, in sensor arrays for detecting an analyte in a fluid. These arrays preferably comprise a plurality of compositionally different chemical sensors. Each sensor comprises at least first and second conductive electrodes electrically coupled to and separated by a chemically sensitive resistive region. The electrodes (which may comprise 2 or more individual units or pairs of units) may be comprised of any convenient conductive material or combination of materials such as, for example, a metal. Preferred metals include copper, silver, platinum, nickel, cadmium, tin, and other materials that may be metals and/or non-metals well known to those of ordinary skill in the art as conductive (e.g. ceramics), and more preferred gold.

The resistive region preferably includes carbon nanotubes in either alone or blended with other chemical species. Preferably, the resistive region between the electrodes is about 5 microns to about 500 microns wide. More preferably, the resistive region is about 40 microns to about 100 microns wide. Most preferably, the resistive region is about 50 to about 80 microns wide.

The resistance of carbon nanotubes changes when exposed to different analytes. For example, the resistance of carbon nanotubes decreases when exposed to oxygen. Consequently, carbon nanotubes may be used in a sensor for determining the presence and concentration of oxygen along with other chemical analytes.

In one embodiment the resistive region includes a coating of carbon nanotubes between electrode regions. The carbon nanotubes can be deposited in the gap between the electrodes in any manner that can apply a uniform distribution of carbon nanotubes. Preferably, the carbon nanotubes are deposited as a layer which can be 100 microns or less. Preferred thickness ranges include 30 microns or less, 20 microns or less, 10 microns or less, and 1 micron or less.

By applying the carbon nanotubes in such a thin layer, the responsiveness of the sensor can be increased. A traditional sensor using carbon black and an organic polymer in the resistive region can require the sensor be exposed to an analyte for several minutes before the analyte is sufficiently absorbed through the thick resistive region to produce a reliable reading. By using a much thinner carbon nanotube layer, the present invention can allow readings in a matter of seconds (e.g. 1 sec, 2 sec, 3 sec, 5 sec, 7 sec, 8 sec, 9 sec, 10 sec) or fractions of seconds (e.g. 0.1 sec, 0.01 sec, 0.001 sec, 0.0001 sec, 0.00001 sec) and at lower concentrations (e.g. 1,000 ppm, 10 ppm, 1 ppm, 0.1 ppm, 0.01 ppm, 1 ppb).

Obtaining a uniform thickness of carbon nanotubes in this thin layer can be difficult. Any gaps in the carbon nanotube layer can cause the resistance of the resistive area to increase significantly. Changes in resistance may be gross or subtle. Gross changes include increases or decreases in resistance of 1 fold, 10 fold, 100 fold, 1000 fold or more. Subtle changes can include changes of 50%, 1%, 0.1%, 0.01%, 0.001%, 0.0001% or less. Thus, a significant feature of the invention is the ability to accurately and reproducibly detect such subtle and gross differences.

There is a geometric relationship between gap size and resistivity. For example, when gap distance doubles, resistivity also doubles. The resistance of the chemically sensitive resistors can be increased by increasing the thickness of the carbon nanotube layer and by decreasing the distance between the electrode regions. Preferably, a coating of nanotubes is deposited in the resistive region to give the resistor an electrical resistivity of from about $10^{-2}$ to about $10^{12}$ Ohms/squared for a given gap region. Absolute Ohms/squared may be from about $10^{-2}$ to about $10^{12}$ Ohms/squared, from about $10^{-1}$ to about $10^6$ Ohms/squared, from about $10^{-1}$ to about $10^4$ Ohms/squared, and from about $10^0$ to about $10^2$ Ohms/squared.

The resistive region of the resistor can include a single layer that contains carbon nanotubes or can include multiple layers some or all of which contain carbon nanotubes (e.g. alternating layers, increasing or decreasing gradient layers). In addition to carbon nanotubes, other layers in the resistive region of the resistor may contain for example organic polymers and blends of organic polymers with conductive materials dispersed within the organic polymer.

Nanotubes are known and have a conventional meaning. (R. Saito, G. Dresselhaus, M. S. Dresselhaus, "Physical Properties of Carbon Nanotubes," Imperial College Press, London U.K. 1998, or A. Zettl "Non-Carbon Nanotubes" Advanced Materials, 8, p. 443 (1996)).

In a preferred embodiment, nanotubes of this invention comprise straight and bent multi-walled nanotubes (MWNTs), straight and bent double-walled nanotubes (DWNTs) and straight and bent single-walled nanotubes (SWNTs), and various compositions of these nanotube forms, chemical modifications of the nanotubes (e.g. metalized, phenolic groups, acid groups, sequences, peptides, side-wall functionalized chemical moieties which may be covalently or noncovalently bonded), and common by-products contained in nanotube preparations such as described in U.S. Pat. Nos. 6,333,016 and 6,645,455, U.S. Patent Application Publication Nos. 20020110513, 20020004028, and 20020086124, and International Application Publication No. WO 01/92381, which are all incorporated herein by reference in their entirety.

The nanotubes of the instant invention preferably have an outer diameter of less than 3.5 nm. In another preferred embodiment, nanotubes of the instant invention have an outer diameter of less than 3.25 nm. In another preferred embodiment, nanotubes of the instant invention have an outer diameter of less than 3.0 nm. In another preferred embodiment, the nanotubes have an outer diameter of about 0.5 to about 2.5 nm. In another preferred embodiment, the nanotubes have an outer diameter of about 0.5 to about 2.0 nm. In another preferred embodiment, the nanotubes have an outer diameter of about 0.5 to about 1.5 nm. In another preferred embodiment, the nanotubes have an outer diameter of about 0.5 to about 1.0 nm. The aspect ratio may be between 10 and 2000.

In a preferred embodiment, the nanotubes comprise single walled carbon-based SWNT-containing material. SWNTs can be formed by a number of techniques, such as laser ablation of a carbon target, decomposing a hydrocarbon, and setting up an arc between two graphite electrodes. For example, U.S. Pat. No. 5,424,054 to Bethune et al. describes a process for producing single-walled carbon nanotubes by contacting carbon vapor with cobalt catalyst. The carbon vapor is produced by electric arc heating of solid carbon, which can be amorphous carbon, graphite, activated or decolorizing carbon or mixtures thereof. Other techniques of carbon heating are discussed, for instance laser heating, electron beam heating and RF induction heating. Smalley (Guo, T., Nikoleev, P., Thess, A., Colbert, D. T., and Smally, R. E., Chem. Phys. Lett. 243: 1-12 (1995)) describes a method of producing single-walled carbon nanotubes wherein graphite rods and a transition metal are simultaneously vaporized by a high-temperature laser. Smalley (Thess, A., Lee, R., Nikolaev, P., Dai, H., Petit, P., Robert, J., Xu, C., Lee, Y. H., Kim, S. G., Rinzler, A. G., Colbert, D. T., Scuseria, G. E., Tonarek, D., Fischer, J. E., and Smalley, R. E., Science, 273: 483-487 (1996)) also describes a process for production of single-walled carbon nanotubes in which a graphite rod containing a small amount of transition metal is laser vaporized in an oven at about 1200° C. Single-wall nanotubes were reported to be produced in yields of more than 70%. U.S. Pat. No. 6,221,330, which is incorporated herein by reference in its entirety, discloses methods of producing single-walled carbon nanotubes which employs gaseous carbon feedstocks and unsupported catalysts.

SWNTs are flexible and aggregate to form ropes of tubes (e.g. U.S. Pat. Nos. 6,183,714; 6,683,783). The formation of SWNT ropes in the coating or film allows the conductivity to be very high, while loading can be very low. Alternatively, layers can be formed that comprise mostly or all carbon nanotubes, or a plurality of layers can alternate with layers with and without nanotubes. Preferably, the carbon nanotubes are acid treated and/or sonic treated before being deposited. Acid treating and sonic treating the carbon nanotubes breaks the carbon nanotubes apart and results in a more uniform carbon nanotube distribution.

The carbon nanotubes can be applied as a layer in the resistive region alone or may be blended with other chemical species and then applied as a layer to increase the chemical sensing abilities of the sensor. The carbon nanotube layer comprises about 0.01% to 1% nanotubes, 5% to 10% nanotubes, 10% to 25% nanotubes, 25% to 50% nanotubes, 50% to 75% nanotubes, 75% to 100% nanotubes, and combinations of these ranges.

The carbon nanotube layer is the resistor and can be applied to a substrate by many conventional and well-known techniques. For example, see the techniques outlined in WO 02/076724, the disclosure of which is hereby incorporated by reference in its entirety. Preferably, the carbon nanotube layer is formed and applied to a substrate such as a dispersion of nanotubes alone in solvents such as, for example, acetone, acetates, nitrites, aldehydes, water, ethers, and alcohols. Additional solvents that can be used include, but are not limited to aliphatic, halogenated (e.g. chloro and fluoro carbons), amines, heterocyclic, aromatic and others well known to those of ordinary skill. The solvent may be removed by normal processes such as air drying, heating or reduced pressure to form the desired film of nanotubes. The layer may be applied by other known processes such as spray painting, dip coating, spin coating, knife coating, kiss coating, gravure coating, screen printing, ink jet printing, pad printing, other types of printing or roll coating.

A dispersion is a composition comprising preferably, but not limited to, a uniform or non-uniform distribution of two or more heterogeneous materials. Those materials may or may not chemically interact with each other or other components of the dispersion or be totally or partially inert to components of the dispersion. Heterogeneity may be reflected in the chemical composition, or in the form or size of the materials of the dispersion.

In one embodiment, the nanotubes are blended with a blending agent. Preferred blending agents include organic and inorganic polymers, ceramics, and liquids which act as a co-continuous phase or interpenetrated network. A more preferred blending agent is an organic polymer. The carbon nanotubes can be suspended or dispersed of particulate in a matrix of nonconductive organic polymer material, the matrix regions separating the carbon nanotubes provide gaps between the nanotubes. The nonconductive polymer gaps range in path length from about 1 to 10,000 angstroms, and preferably range in path length from about 10 to 1,000 angstroms, usually on the order of 100 angstroms. The path length and resistance of a given gap is not constant but rather is believed to change as the nonconductive organic polymer of the region absorbs, adsorbs or imbibes an analyte. Accordingly the dynamic aggregate resistance provided by these gaps in a given resistor is a function of analyte permeation of the nonconductive regions.

Accordingly, if the carbon nanotubes are suspended in an organic polymer or other chemical species that responds to analytes, the resistive response of a sensor using the nanotubes and polymer resistor is dictated by both the response of the nanotubes and the specific polymer used. By using different polymers in different resistive elements, the sensors can be made to respond to a wide variety of analytes.

A wide variety of nonconductive organic polymer materials can be used. Table 1 provides exemplary nonconductive organic polymer materials that can be used; blends and copolymers, such as of the polymers listed here, may also be used. Combinations, concentrations, blend stoichiometries, percolation thresholds, etc. are readily determined empirically by fabricating prototype resistors (e.g. chemiresistors) as described below.

TABLE 1

| Major Class | Examples |
| --- | --- |
| Main-chain carbon polymers | poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitrites), poly(vinyl esters), poly(styrenes), poly(aryienes), etc. |
| Main-chain acyclic heteroatom polymers | poly(oxides), poly(carbonates), polylesters), poly(anhydrides), poly(urethanes), poly(sulfonates), poly(siloxanes), poly(sulfides), poly(thioesters), poly(sulfones), poly(sulfonamides), poly(amides), poly(ureas), poly(phosphazenes), poly(silanes), poly(silazanes), etc. |
| Main-chain heterocyclic polymers | poly(furan tetracarboxylic acid diimides), poly(benzoxazoles), poly(oxadiazoles), poly(benzothiazinophenothiazines), poly(benzothiazoles), poly(pyrazinoquinoxalines), poly(pyromenitimides), poly(quinoxalines), |

TABLE 1-continued

| Major Class | Examples |
| --- | --- |
| | poly(benzimidazoles), poly(oxindoles), poly(oxoisoindolines), poly(dioxoisoindolines), poly(triazines), poly(pyridazines), poly(piperazines), poly(pyridines), poly(piperidines), poly(triazoles), poly(pyrazoles), poly(pyrrolidines), poly(carboranes), poly(oxabicyclononanes), poly(dibenzofurans), poly(phthalides), poly(acetals), poly(anhydrides), carbohydrates, etc. |

In addition to nonconductive polymers, the carbon nanotubes may be blended with other conducting species, to change the resistance of the resistive region. In addition, some conductive materials may also be used to contribute to the dynamic aggregate resistance as a function of analyte permeation (e.g. when the conductive material is a conductive organic polymer such as polyprryole). Table 2 discloses some conducting materials that may be blended with the carbon nanotubes.

TABLE 2

| Major Class | Examples |
| --- | --- |
| Organic Conductors | conducting polymers (poly(anilines), poly(thiophenes), poly(pyrroles), poly(acetylenes), etc.)), carbonaceous materials (carbon blacks, graphite, coke, $C_{60}$, etc.), charge transfer complexes (tetramethylparaphenylenediamine-chloranile, alkali metal tetracyanoquinodimethane complexes, tetrathiofulvalene halide complexes, etc.), etc. |
| Inorganic Conductors | metals and metal alloys (Ag, Au, Cu, Pt, AuCu alloy, etc.), highly doped semiconductors (Si, GaAs, InP, $MoS_2$, $TiO_2$, etc.), conductive metal oxides ($In_2 O_3$, $SnO_2$, $Na_x Pt_3 O_4$, etc.), superconductors ($YBa_2 Cu_3 O_7$, $Tl_2 Ba_2 Ca_2 Cu_3 O_{10}$, etc.), etc. |
| Mixed inorganic/organic Conductor | Tetracyanoplatinate complexes, Iridium halocarbonyl complexes, stacked macrocyclic complexes, etc. |

Preferred sensor arrays have a predetermined inter-sensor variation in the structure or composition of the resistive regions. The variation may be quantitative and/or qualitative. For example, the concentration of a nonconductive organic polymer in the blend can be varied across sensors. Alternatively, a variety of different organic polymers may be used in different sensors. An electronic nose for detecting an analyte in a fluid is fabricated by electrically coupling the sensor leads of an array of compositionally different sensors to an electrical measuring device. The device measures changes in resistivity at each sensor of the array, preferably simultaneously and preferably over time. Frequently, the device includes signal processing means and is used in conjunction with a computer and data structure for comparing a given response profile to a structure-response profile database for qualitative and quantitative analysis. Typically such a nose comprises at least 10, usually at least 100, and often at least 1000 different sensors though with mass deposition fabrication techniques described herein or otherwise known in the art, arrays of on the order of at least $10^6$ sensors are readily produced. Those of ordinary skill can create arrays of at least $10^8$, at least $10^{10}$, at least $10^{12}$, or more.

In operation, each resistor provides a first electrical resistance between its conductive leads when the resistor is contacted with a first fluid comprising a chemical analyte at a first concentration, and a second electrical resistance between its conductive leads when the resistor is contacted with a second fluid comprising the same chemical analyte at a second different concentration. The fluids may be liquid or gaseous in nature. The first and second fluids may reflect samples from two different environments, a change in the concentration of an analyte in a fluid sampled at two time points, a sample and a negative control, etc. The sensor array necessarily comprises sensors which respond differently to a change in an analyte concentration, i.e. the difference between the first and second electrical resistance of one sensor is different from the difference between the first second electrical resistance of another sensor.

In a preferred embodiment, the temporal response of each sensor (i.e. resistance as a function of time or response time) is recorded. Response times of less than a minute are preferred, more preferred are response times of less than 30 seconds and less than 10 seconds and less than 5 seconds. Even more preferred are response times of less than 1 second, less than 0.1 seconds, less than 0.01 seconds, less than 0.001 seconds, and less than 0.0001 seconds. The temporal response of each sensor may be normalized to a maximum percent increase and percent decrease in resistance which produces a response pattern associated with the exposure of the analyte. By iterative profiling of known analytes, a structure-function database correlating analytes and response profiles is generated. Unknown analyte may then be characterized or identified using response pattern comparison and recognition algorithms. Accordingly, analyte detection systems comprising sensor arrays, an electrical measuring devise for detecting resistance across each chemiresistor, a computer, a data structure of sensor array response profiles, and a comparison algorithm are provided. In another embodiment, the electrical measuring device is an integrated circuit comprising neural network-based hardware and a digital-analog converter (DAC) multiplexed to each sensor, or a plurality of DACs, each connected to different sensor(s).

A wide variety of analytes and fluids may be analyzed by the disclosed sensors, arrays and noses so long as the subject analyte is capable generating a differential response across a plurality of sensors of the array. Analyte applications include broad ranges of liquids and gasses, including but not limited to, chemical classes such as organics such as alkanes, alkenes, alkynes, dienes, alicyclic hydrocarbons, arenes, alcohols, ethers, ketones, aldehydes, carbonyls, water and humidity, gels and aerosols, carbanions, polynuclear aromatics and derivatives of such organics, carbon dioxide gas, atmosphere, oxygen and/or nitrogen gas, e.g. halide derivatives, etc., biomolecules such as sugars, isoprenes and isoprenoids, fatty acids and derivatives, etc. (many of which are also useful as the solvent), and combinations thereof. Compounds that are typically detectable in gaseous form include sarin, nerve gas, mustard gas, dispersed biological materials such as viruses, bacteria, smallpox, spores, etc. (e.g. gaseous, aerosol and liquid weapons of mass destruction) Sensors can also be imbedded in the body or other difficult to monitor locations, providing results through wireless connections. Accordingly, commercial applications of the sensors, arrays and noses include environmental toxicology and remediation, biomedicine, materials quality control, food and agricultural products monitoring, etc.

The general method for using the disclosed sensors, arrays and electronic noses, for detecting the presence or amount (quantitative or qualitative detection) of an analyte in a fluid (i.e. gas or liquid) involves resistively sensing the presence of an analyte in a fluid with a chemical sensor comprising first and second conductive leads electrically coupled to and separated by a chemically sensitive resistor as described above by measuring a first resistance between the conductive leads when the resistor is contacted with a first fluid comprising an analyte at a first concentration and a second different resistance when the resistor is contacted with a second fluid comprising the analyte at a second different concentration. By comparing resistances, or even a single resistance with a known value for the absence of the analyte, the presence, absence and/or amount of the analyte or combination of analytes can be determined.

resistive region. The gold electrode region is formed by printing and is patterned to leave the serpentine shaped area free of gold. The serpentine shaped gap between the gold electrodes is the resistive region. A spray coating of pure nanotubes was deposited across the entire surface of the chemically sensitive resistor but are only functional in the serpentine gap between the gold electrodes. The nanotubes have been acid treated and sonic treated prior to deposition to break the nanotubes apart. The nanotubes are deposited in a solvent.

Table 3 below shows the results for a number of chemically sensitive resistors. Each spot is a single chemically sensitive resistor element. The thickness of the carbon nanotube region varies from spot to spot. As can be seen from the table, a wide range of resistance values can be obtained by varying the deposition of the carbon nanotube layer.

TABLE 3

| | Substrate number and side, (Resistivity in Ohms) | | | | | | | |
|---|---|---|---|---|---|---|---|---|
| Spot Number | 1A | 1B | 2A | 2B | 3A | 3B | 4A | 4B |
| 1 | 9690 | 9300 | 177000 | 230000 | 150 | 134 | 5100 | 4100 |
| 2 | 11000 | 5700 | 191000 | 297000 | 376 | 195 | 5600 | 8100 |
| 3 | 10300 | 5000 | 143000 | 156000 | 233 | 264 | 6600 | 5300 |
| 4 | 7800 | 3600 | 152000 | 127000 | 205 | 162 | 7100 | 4600 |
| 5 | 6800 | 3700 | 100000 | 165000 | 141 | 169 | 6300 | 4700 |
| 6 | 5300 | 2800 | 84000 | 108000 | 194 | 171 | 11100 | 3200 |
| 7 | 4100 | 2800 | 68000 | 93000 | 136 | 170 | 5900 | 3400 |
| 8 | 4200 | 3100 | 111000 | 102000 | 121 | 158 | 5200 | 3300 |
| 9 | 3900 | 3100 | 51000 | 104000 | 135 | 165 | 6800 | 4200 |
| 10 | 3300 | 3100 | 110000 | 85000 | 159 | 157 | 6800 | 3700 |
| 11 | 3100 | 3700 | 63000 | 104000 | 130 | 205 | 6900 | 4500 |
| 12 | 3900 | 3700 | 138000 | 206000 | 166 | 195 | 4100 | 4000 |
| 13 | 4300 | 4000 | 74000 | 102000 | 162 | 222 | 3600 | 3800 |
| 14 | 4200 | 5300 | 91000 | 112000 | 192 | 210 | 4500 | 5000 |
| 15 | 4600 | 6100 | 85000 | 103000 | 266 | 203 | 9000 | 4700 |
| 16 | 6300 | 7800 | 94000 | 155000 | 271 | 230 | 8800 | 4700 |
| Average | 5799 | 4550 | 108250 | 140563 | 190 | 188 | 6463 | 4456 |
| STD | 2587 | 1887 | 41156 | 59029 | 68 | 33 | 1939 | 1152 |
| Witness Substrate (Ohms/Square) | 55200 | 55400 | 366000 | 925000 | 4030 | 2570 | 33100 | 48100 |

In addition, testing can identify resistance values that are specific for certain analytes. Thus, sensors can be programmed to detect only certain resistances for detection of only certain analytes. Alternatively, a variety of resistances can be programmed to a sensor to detect a wide variety and combination of different analytes.

The following examples illustrate embodiments of the invention, but should not be viewed as limiting the scope of the invention.

EXAMPLES

Following is a description of the method of making a chemically sensitive resistor according to this invention.

Coating resistivity can be controlled during the spray coating process. Spray coating is a preferred method of depositing the carbon nanotube coating since the carbon nanotubes are broken apart during the spray coating process resulting in a more uniform carbon nanotube distribution in the coating. A substrate can be mounted in the deposition chamber for the spray coating process.

A chemically sensitive resistor can have a gold electrode region that is separated into section by a serpentine patterned Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims.

The invention claimed is:

1. A chemically sensitive resistor comprising:
   a resistive region comprising carbon nanotubes; and
   a conducting electrode on a side of the resistive region,
   wherein the resistor measures a change in resistance of the carbon nanotubes from a known baseline resistance upon exposure to an analyte.

2. The resistor of claim 1, wherein the resistive region comprises only carbon nanotubes.

3. The resistor of claim 1, wherein the resistive region comprises a polymer that swells or reacts to the analyte.

4. The resistor of claim 1, wherein the carbon nanotubes are single-walled carbon nanotubes.

5. The resistor of claim 1, which comprises two conducting electrodes.

6. The resistor of claim 5, wherein the two conducting electrodes are on opposite sides of the resistive region.

7. The resistor of claim 1, wherein the conducting electrode comprises gold.

8. The resistor of claim 1, wherein the change in resistance from the known baseline resistance of the resistive region comprises 20% or less.

9. The resistor of claim 1, wherein the change in resistance from the known baseline resistance of the resistive region comprises 0.001% or less.

10. The resistor of claim 1, wherein the analyte is selected from the group consisting of organics, alkanes, alkenes, alkynes, dienes, alicyclic hydrocarbons, arenas, alcohols, ethers, ketones, aldehydes, carbonyls, water, humidity, gels, aerosols, carbanions, polynuclear aromatics and derivatives thereof, carbon dioxide gas, atmosphere, oxygen, nitrogen, halides and halide derivatives, biomolecules, sugars, isoprenes and isoprenoids, fatty acids and derivatives and combinations thereof.

11. The resistor of claim 1, wherein the analyte is selected from the group consisting of sarin gas, nerve gas, mustard gas, dispersed biological materials, viruses, bacteria, smallpox, spores, gaseous, aerosol and liquid weapons of mass destruction, and combinations thereof.

12. The resistor of claim 1, wherein the known baseline resistance is a resistance with a known value for absence of the analyte.

13. The resistor of claim 1, wherein the resistive region is inhibited from undergoing a change in resistance upon exposure to the analyte.

14. The resistor of claim 13, wherein the inhibited resistive region comprises alternating layers of carbon nanotubes, organic polymers, conductive materials or combinations thereof.

15. The resistor of claim 14, wherein the alternating layers further comprise chemical species that resistively respond to analytes, blending agents, matrices of non-conductive polymer materials or combinations thereof.

16. The resistor of claim 13, wherein the inhibited resistive region comprises varying thicknesses of layers of carbon nanotubes.

* * * * *